United States Patent [19]

Rouanne

[11] Patent Number: 5,104,452
[45] Date of Patent: Apr. 14, 1992

[54] METHOD FOR METERING MONOCALCIUM SACCHARATE INTO A SUGARED JUICE

[75] Inventor: Francois Rouanne, Lille, France

[73] Assignee: Fives-Cail Babcock, Montreuil, France

[21] Appl. No.: 665,254

[22] Filed: Mar. 6, 1991

[30] Foreign Application Priority Data

Mar. 8, 1990 [FR] France ................ 90 02939

[51] Int. Cl.⁵ ............................ C13D 1/14; C13J 1/04
[52] U.S. Cl. ....................... 127/42; 127/46.1; 127/47; 127/48; 127/55
[58] Field of Search ................ 127/46.1, 47, 48, 55, 127/42

[56] References Cited

U.S. PATENT DOCUMENTS

| | | | |
|---|---|---|---|
| 1,256,952 | 2/1918 | Tiemann | 127/47 |
| 2,000,202 | 5/1935 | Vazquez | 127/47 |
| 2,281,025 | 4/1942 | Cottrell et al. | 127/47 |

Primary Examiner—Theodore Morris
Assistant Examiner—P. L. Hailey
Attorney, Agent, or Firm—Collard, Roe & Galgano

[57] ABSTRACT

There is provided a method of metering monocalcium saccharate into a sugared juice. The process includes taking a sample of the juice to be analyzed, diluting the sample with alcohol in order to form a precipitate, separating the precipitate by filtration, dissolving the precipitate in deionized water, acidifying the solution obtained by the addition of phosphoric acid and metering the saccharose into the said solution. The method is usable, in particular, in sugar refining in the production of sugared juices by the alkaline diffusion process.

5 Claims, No Drawings

METHOD FOR METERING MONOCALCIUM SACCHARATE INTO A SUGARED JUICE

BACKGROUND OF THE INVENTION

1. Field of the Invention

The present invention relates to a method for metering monocalcium saccharate into sugared juices usable, in particular, in beet sugar factory in the production of sugared juices by the alkaline diffusion process. 2. The Prior Art It is known that in this process sugar beet chips are subjected to a prior calcification process by means of a juice containing monocalcium saccharate. In order to control this process, it is important to know the content in monocalcium saccharate of the juice used, at least at the beginning and end of the process. Until now there was no method of metering this compound into a sugared juice.

SUMMARY OF THE INVENTION

It is an object of the present invention to remedy this lack of metering.

The above object is accomplished in accordance with the present invention by a method of metering the monocalcium saccharate which comprises taking a sample of the juice to be analyzed, diluting this sample with alcohol in order to form a precipitate, separating the precipitate by filtration, dissolving the precipitate in deionized water, acidifying the solution obtained by adding phosphoric acid and metering the saccharose into the said solution.

The alcohol used to dilute the sample can be miscible with water and can be non-toxic to animals, and will preferably be ethanol.

The saccharose will be metered by polarimetry, by a means of a saccharimeter, after having subjected the solution to a defecation following the method usually employed for the metering of the saccharose into sugar juices.

Other objects and features of the present invention will become apparent from the following detailed description considered in connection with the following example which discloses one embodiment of the present invention. It should be understood, however, that the example is designed for the purpose of illustration only and not as a definition of the limits of the invention.

DETAILED DESCRIPTION OF PREFERRED EMBODIMENTS

A sample of 10 ml of the juice to be analyzed is taken and it is poured into a 100 ml phial, then the filling of the phial up to 100 ml is completed with ethanol.

A precipitate is formed, made up essentially, but not exclusively, of monocalcium saccharate, which is separated from the liquid phase by filtration in a vacuum in a membrane filter, for example a MILLIPORE (registered trademark) filter No. AT 200 - 47 -00, which was previously weighed.

The precipitate retained by the membrane of the filter is washed with alcohol and then dried with the filter in an oven for one to two hours. The filter is then weighed in order to determine the weight of the precipitate.

The precipitate is then dissolved in 50 ml of deionized water, the solution obtained is acidified up to pH 4 by the addition of 3 N phosphoric acid and deionized water is added in order to obtain 100 ml of a solution containing saccharose and calcium phosphate.

This solution is subjected to a defecation and the saccharose it contains is metered by polarimetry in accordance with the known method usually employed for the metering of saccharose in sugar refinery juices.

The weight of saccharose, Ps in grams, contained in the 10 ml of the sample is given by the formula:

$Ps$ = Reading of saccharimeter × coefficient of standardization.

In France, the coefficient of standardization is equal to 0.26. In the United States, this coefficient is 0.26.

The weight of monocalcium saccharate Pm in grams contained in the 10 ml of the sample will be calculated by the formula:

$$Pm = Ps \times 382/342 = Ps \times 1.117$$

The weight of lime Pca in grams in the 10 ml which reacted with the saccharose will be $$Pca = 0.1047\ Pm = 0.1170$$

For verification, the calcium may be metered into the solution by the use of an atomic absorption spectrophotometer, and it may be ensured that the saccharose/calcium molar ratio is indeed equal to 1. The calcium may also be metered by alkalinity, a well-known method of metering in beet sugar factory.

While only a single embodiment of the present invention has been shown and described, it is to be understood that many changes and modifications may be made thereunto without departing from the spirit and scope of the invention as defined in the appended claims.

What is claimed is:

1. Method of metering of monocalcium saccharate into a sugared juice comprising:
   providing a sample of the juice to be analyzed;
   diluting the sample with an alcohol in order to form a precipitate;
   separating the precipitate by filtration;
   dissolving the precipitate in deionized water to form a solution;
   acidifying the solution obtained by adding phosphoric acid;
   defecating said solution; and
   metering by polarimetry the saccharose in the said solution.

2. Method of metering in accordance with claim 1, comprising diluting the sample with said alcohol to approximately 9 times its volume.

3. Method of metering in accordance with claim 1, comprising diluting the sample with ethanol.

4. Method of metering in accordance with claim 1, comprising acidifying the solution until the pH of the said solution is about 4.0 after acidification.

5. Method of metering of monocalcium saccharate into a sugared juice comprising:
   providing a sample of the juice to be analyzed;
   diluting the sample with an alcohol in order to form a precipitate;
   separating the precipitate by filtration;
   dissolving the precipitate in deionized water to form a solution;
   acidifying the solution obtained by adding phosphoric acid;
   metering the saccharose in the said solution;
   metering the calcium into the said solution; and
   checking to determine that the saccharose/calcium molar ratio is equal to 1.

* * * * *